United States Patent
Turner

(10) Patent No.: US 10,871,787 B2
(45) Date of Patent: Dec. 22, 2020

(54) INDICATOR DEVICE AND SYSTEM

(71) Applicant: Spectrum Medical Ltd., Gloucester (GB)

(72) Inventor: Stephen Turner, Gloucestershire (GB)

(73) Assignee: Spectrum Medical Ltd., Gloucester (GB)

( * ) Notice: Subject to any disclaimer, the term of this patent is extended or adjusted under 35 U.S.C. 154(b) by 133 days.

(21) Appl. No.: 16/021,433

(22) Filed: Jun. 28, 2018

(65) Prior Publication Data
US 2019/0001047 A1 Jan. 3, 2019

(30) Foreign Application Priority Data
Jul. 3, 2017 (GB) .................................. 1710664.2

(51) Int. Cl.
G05D 7/06 (2006.01)
A61M 1/36 (2006.01)

(52) U.S. Cl.
CPC ......... *G05D 7/0635* (2013.01); *G05D 7/0676* (2013.01); *A61M 1/3666* (2013.01);
(Continued)

(58) Field of Classification Search
CPC .... A61M 2205/3334; A61M 2205/505; A61M 2205/583; A61M 2205/584;
(Continued)

(56) References Cited

U.S. PATENT DOCUMENTS 5,254,977 A * 10/1993 MacDonald ............. G09G 5/06
345/538
7,867,159 B2 * 1/2011 Dolecek .............. A61M 1/3696
210/512.1
(Continued)

FOREIGN PATENT DOCUMENTS

EP 0 828 526 3/1998
EP 1 668 556 6/2006
(Continued)

OTHER PUBLICATIONS

European Patent Office, Search Report for Application No. EP 18 18 0534, dated Oct. 19, 2018, 2 pages.
(Continued)

*Primary Examiner* — Chun Cao
(74) *Attorney, Agent, or Firm* — Sunstein LLP

(57) ABSTRACT

A flow control system of a clinical perfusion system comprises flow control devices 110, such as pumps, valves and/or clamps, capable of controlling a fluid flow rate according to flow rate parameters from the flow control system. The flow control system comprises an indicator arrangement including a device indicator 122a, 122b on each flow control device 110 capable of providing a plurality of indications. The device indicators 122a, 122b are controllable by the flow control system to indicate an active condition of the flow control device 110 independently of the flow rate parameters. This allows the indication provided by the device indicator 122a, 122b to be adjusted for different clinical environments, and to provide colour indications that match the colour range discernible by users affected by colour vision deficiency.

14 Claims, 4 Drawing Sheets

(52) U.S. Cl.
CPC .............. *A61M 2205/3334* (2013.01); *A61M 2205/505* (2013.01); *A61M 2205/583* (2013.01); *A61M 2205/584* (2013.01); *A61M 2205/6063* (2013.01); *A61M 2205/6081* (2013.01)

(58) Field of Classification Search
CPC .......... A61M 2205/587; A61M 1/3666; A61M 1/3653; G05D 7/0676; G05D 7/0635
USPC ....................................................... 700/282
See application file for complete search history.

(56) References Cited

U.S. PATENT DOCUMENTS

| | | |
|---|---|---|
| 9,393,357 B2* | 7/2016 | Ellingboe ........... A61M 1/3621 |
| 9,770,554 B2* | 9/2017 | Dollar ................... A61M 5/172 |
| 2008/0033361 A1 | 2/2008 | Evans et al. |
| 2008/0072902 A1 | 3/2008 | Setzer et al. |

FOREIGN PATENT DOCUMENTS

| | | | |
|---|---|---|---|
| EP | 2371411 A1 * | 10/2011 | ........ A61M 16/0875 |
| EP | 2371411 A1 | 10/2011 | |
| WO | WO 2014/151930 | 9/2014 | |
| WO | WO 2105/153254 | 10/2015 | |

OTHER PUBLICATIONS

United Kingdom Intellectual Property Office, Search Report—Application No. GB 1710664.2, dated Jan. 30, 2018, 3 pages.
European Patent Office, Examination Report for Application No. EP 18 180 534.2, dated Jan. 10, 2020, 7 pages.

* cited by examiner

INDICATOR DEVICE AND SYSTEM

PRIORITY

This patent application claims priority from UK Patent Application No. GB 1710664.2, filed Jul. 3, 2017, entitled "Indicator Device and System", and naming Stephen Turner as inventor, the disclosure of which is incorporated herein, in its entirety, by reference.

FIELD OF THE INVENTION

The present invention relates to an indicator device and system used in a flow control system comprising multiple flow control devices, specifically for use in extracorporeal perfusion systems. More specifically, the present invention relates to an indicator arrangement facilitating the management of multiple flow control devices for users with colour vision deficiency.

BACKGROUND

Extracorporeal perfusion is used to substitute heart and lung functionality during medical procedures. An extracorporeal perfusion system comprises a blood-pumping mechanism and an oxygenation mechanism, to circulate and re-oxygenate blood extracorporeally (outside a patient's body). Extracorporeal perfusion is a highly complex procedure and requires coordinated management of supply and removal of oxygenation gases, recovery and return of patient blood, management of safe blood reservoir volumes, management of blood pressure levels, management of blood clotting issues, management of controlled heart-beat-suppression, and management of infection risks, to name only a few issues.

Perfusion technology has undergone significant development in recent years. It is more and more common for the various apparatus related to clinical perfusion to be provided as an integrated system. For instance, an integrated perfusion system may be provided in the form of a single trolley comprising subsystems including a blood treatment system, oxygenation gas (supply and exhaust) management system, cardioplegia system (cardioplegia=controlled heart-beat suppression) and other subsystems.

Such integrated systems comprise several flow passages (tubes) controlled by mechanical flow control devices (pumps, valves or clamps), whose functioning is critical to a perfusion procedure, because the pump control affects the flow rates and operating pressures of fluids in the system and of fluids circulated to a patient.

EP2371411A1 discloses a visual status indicator for providing a status indication of a fluid transported through a patient circuit between a medical device and a patient, and a light source for providing a light signal in dependence on a measured status of the fluid transported through the patient circuit.

The present invention seeks to provide improved monitoring methods used during perfusion management.

SUMMARY OF THE EMBODIMENTS

In accordance with a first aspect of the present invention, there is provided a flow control system as defined in claim 1.

The flow control system comprises one or more flow control devices of a clinical perfusion system, each flow control device capable of controlling, according to flow rate parameters provided by the flow control system, a flow rate of a fluid to be provided. The flow control system further comprises an indicator arrangement. The indicator arrangement includes a device indicator on each flow control device. The one or more device indicators are capable of providing a plurality of indications. The one or more device indicators are controllable by the flow control system to provide one indication of the plurality of indications to indicate an active condition of the flow control device. The one or more device indicators are configurable by the control system independently of the flow rate parameter, thereby to allow the indication provided by the device indicator to be adjusted for different clinical environments regardless of flow rate parameters issued to the one or more flow control devices.

The flow control system may be, in particular, the control system of an extracorporeal perfusion system, wherein a controller of the system is provided to issue commands to flow control devices. A flow control device is considered herein a mechanical flow control device, such as a device in mechanical contact with a fluid line to mechanically influence the flow rate of a fluid in response to an actuation signal. The flow control device may be issued with a flow rate parameter according to a set point. The flow control device may be a pump, such as a peristaltic (roller) pump or a centrifugal pump. The flow control device may be a valve or a clamp, such as a gradually actuatable clamp. A gradually actuatable clamp is understood to be acting on a flexible tube to restrict flow. The flow control device is controlled by setting the flow parameter via the flow control system, for instance, to set a pump rotation speed or clamp position to effect a flow rate.

The flow rate parameters may correspond to a set point for the flow control device. To provide examples, a pump may be set to pump at a flow rate of 2 lpm, or an actuatable clamp may be set to restrict a flow rate to no more than 2 lpm.

The indicator arrangement is an arrangement suitable for indicating one or more of several controller conditions of a flow control device. For instance, the flow control device may be set to operate at a flow rate below or above a threshold and the indicator arrangement may indicate that the flow rate is either below or above said threshold (for instance, the indicator may provide a first signal when below a threshold and a second signal when above a threshold). The indicator arrangement may indicate that the pump is active. An active status may include a status in which the flow control device is awaiting a command but not operating to modulate flow (e.g., turned on but not pumping).

In accordance with the invention, the indicator arrangement is configured to change the device indication independently of the flow rate (speed) of the fluid. The device indication may include a first indication that a particular flow control device is in setup mode, while a set point flow rate is entered into the system, and a second indication that the particular flow control device is in an operational mode, in which it is operational to match the set point. The device indication may be a specific colour to facilitate identifying a pump. The ability to change the device indication independently of a flow property of the fluid allows the device indication to be set according to a colour range discernible by a user with colour vision deficiency (colour blindness).

The device indicator is located on the flow control device. The flow control device may be a separate component, located some distance apart from an input interface or from other flow control devices of the same flow control system. The arrangement allows a flow control device to indicate a status, for instance that the particular flow control device is currently in a setup mode or in an operational mode.

Conventionally, set points for different flow control devices are displayed on a display associated with an input interface. This may be a touch screen comprising both the input interface and the set point display. In a clinical scenario it may be desirable to be able to quickly check, visually, while operating the input interface, that a particular flow control device actually responds to a set point, i.e., a user (a perfusionist) would operate the input interface and perhaps quickly glance at the flow control device that mechanically influences (causes or restricts) a flow rate in a fluid line.

Modern integrated systems may comprise several flow control devices (pumps, valves and clamps) and so it is in practice not that easy to quickly focus on a pump. By providing device indicators on the flow control devices, the device indicators are located where the flow control devices are installed. As such, a device indicator may complement a set point display on an input interface that may be remote from the flow control device, or visible from a different direction than the flow control device. The indicator arrangement may comprise a visual indicator.

In some embodiments, the device indicator is capable of displaying a plurality of colours, and the device indicator can be controlled by the flow control system to display one of the colours. The indicator arrangement may comprise a moving element such as a rotor or pointer.

In some embodiments, the device indicator comprises one or more solid state lighting devices, such as LEDs.

This may be multi-colour light emitting diodes (LEDs), such as a multi-colour LED that can emit visual light in practically any colour. It will be understood that a LED will be comprised of components emitting at specific, limited number of wavelengths (e.g., a wavelength constituting a 'red', a 'green' and a 'blue' colour) that are combined at different intensities to provide a macroscopically uniform colour, e.g., a purple light may be achieved by emitting red and blue components. It is further understood that the amount or intensity of an LED light is not necessarily achieved by altering a light emission intensity, but by pulse width (time-duration) modulated pulses. For the purposes of the present disclosure a multi-coloured LED is a device that is capable of displaying a plurality of colours (e.g., a red, purple, or yellow light) and that can be controlled to provide light emission that will be perceived as one of these colours by a user.

In some embodiments, the indicator arrangement is configured to indicate the flow direction of the fluid to be provided.

The device indicator may indicate the flow direction of the fluid to be provided. The flow direction may be a forward or reverse flow direction. E.g., if the flow control device is constituted by a pump with a pump inlet and a pump outlet, the device indicator may be configured to indicate forward flow (flow in the inlet-to-outlet direction) and to indicate reverse flow (flow in the outlet-to-inlet direction).

In some embodiments, one or more flow control devices comprise a first device indicator and a second device indicator, to indicate the flow direction by using the first device indicator to provide a first device indication and the second device indicator to provide a second device indication, wherein the second device indication differs from the first device indication.

It will be understood that the difference between the first device indication and the second device indication may suffice to indicate a flow direction.

In some embodiments, the second device indication differs from the first device indication by providing one or more of a different intensity, a different colour, and/or a different time-dependent signal.

For instance, the first device indicator may be brighter (higher intensity) than the second device indicator.

For instance, the first device indicator may provide an indication using a first colour and the second device indicator may provide an indication using a second colour different than the first colour.

For instance, the first device indicator may be activated for a first period of time and the second device indicator is consecutively activated and deactivated during the first period of time. I.e., the first device indicator is continuously on and the second device indicator flashes on and off.

The different visual appearance may be provided by a combination of two or more of any of the above, e.g., by different colours of different intensity or of different flashing patterns.

The indicator arrangement may comprise two LEDs, positioned one each at one end of a passage of the flow control device (e.g., one LED at a pump inlet and one LED at a pump outlet). By "at one end", it is understood that the LEDs are positioned such that they can be associated with the end. Each LED may be positioned on the outlet of a passage. The LEDs may be positioned spread apart along the passage such that one LED is closer to a first end of the passage and another LED is closer to a second end of the passage. Which end of a passage constitutes an inlet or outlet depends on the flow direction. The LED that is upstream in forward flow direction will be downstream in reverse flow direction. The flow direction through the pump may be indicated by activating the upstream LED continuously and by flashing the downstream LED, i.e., such that the downstream LED is activated and deactivated while the upstream LED is lit. Conversely, the system may be set up such that the downstream LED is lit continuously and the upstream LED flashes.

This facilitates the indication of a flow direction with as few as two device indicators per flow control device, while also allowing another device indicator property (e.g., the indicator colour) to be changed independently of a flow rate parameter issued to the flow control device. This is helpful in a medical setting, in which a pump may be visible and it may be discernible that the pump is running, but it may not be straightforward to discern the flow direction, or at least it may not be straightforward to discern the flow direction when only briefly glancing at the flow control device.

With regard to a LED light being 'on', herein this means the appearance of a LED to a user. It is understood that a LED that is continuously 'on' may, at driver level, be pulse width modulated (on and off) at a kHz frequency (e.g., several 10,000 times per second) and will to a human eye appear continuously on. An LED that appears flashing is understood herein as a LED that is turned on and off in a manner that is discernible by eye by a human user.

In some embodiments, the indicator arrangement comprises a controller comprising a processor and software instructions implemented by the processor.

In some embodiments, the flow control system comprises an input interface, the input interface comprising input elements permitting flow control parameters to be set for the one or more flow control devices, thereby to control said flow rates of the fluids to be provided.

The input interface may be provided in the form of a console or in the form of a touch screen with a graphical user interface. Touch screens are more and more established because of their ease of use and because of the possibility to rearrange the user interface layout by programming. Traditional consoles are popular in the medical setting because certain input elements, such as turnable knobs, allow a setting to be changed at various speeds (e.g., by quickly or slowly turning the knob). Turnable knobs also provide haptic feedback.

In some embodiments, the input interface comprises one or more input elements for each one of the flow control devices.

A flow control device may be controllable by multiple input elements, e.g., the same flow control device may be controllable by a touch screen (GUI) interface and by a mechanical input element such as a knob.

In some embodiments, the indicator arrangement comprises an input interface indicator to provide an input status indication of the flow control parameters set by the one or more input elements.

For instance, the control interface for a particular flow control device may display a set point flow rate corresponding to the particular flow control device.

In some embodiments, the indicator arrangement is configured to use an input status indication for the one or more input elements that matches the indication provided by the device indicator of the flow control device.

For instance, the set point flow rate may be displayed in a display field that has the same colour as the device indication. This facilies a quick visual check that an input relates to a particular pump, particularly in the context of perfusion systems that comprise a plurality of pumps, because a flow control device (e.g., pump, valve or clamp) can be quickly identified by the device indication, e.g., when glancing away from the input interface.

In some embodiments, the input interface comprises a configuration identifying an input element by a colour.

In some embodiments, the flow control system comprises a lookup table comprising data for colour control signals to better match colour tones of the one or more device indicators with corresponding colour tones of the input interface indicators, thereby to provide a better colour match between indicator arrangements using different indicator device types.

In practice, different indicator devices may be used for the indicator arrangements. E.g., multi-colour LEDs may constitute the device indicators of pumps and a computer screen display may constitute the input interface indicator. The colours tones of these different indicator devices are not necessarily identical, e.g. the visual appearance provided by a 100% blue LED light installed on a pump may not correspond to the visual appearance provided by a [0,0,255] RGB value of the computer screen. The appearance of such colours when generated by different light sources may differ noticeably.

The inventors have discovered that a better colour match can be established in practice by driving, or aligning, colour values via a look-up table that allows indicators of an indicator arrangement to be matched more closely across different systems. For instance, an LED may be set to 87% of maximum blue intensity and a computer screen may be set to an RGB value of [40,0,240] to match the same colour. The look-up table helps to ensure that the same appearance colour is used for the device indicators and for the input interface indicators. The look-up table may comprise adjustment data for settings affecting the appearance of an indicator device, such as hue, brightness, and others. The look-up table may comprise adjustment values for a plurality of devices, e.g., for flow control devices, for a touch screen, and for an input console.

In some embodiments, the input interface comprises a touch screen.

The input status indication may match the device indication. For instance, the controller status indication may include a first indication that a particular flow control device is in setup mode and a second indication that the flow control device is in an operational mode. The input status indication is controlled to match the device indication. For instance, a multi-colour LED of a flow control device (pump) may light up in a green colour to indicate a first condition and in a blue colour to indicate a second condition. The input status indication will in that example correspondingly be applied to the input element for the flow control device, i.e., to a green colour or blue colour, correspondingly, such that both the input element and the device indicator have matching colours.

The configuration provides a dynamic indication system that facilitates the monitoring of conditions of different components of a flow control system.

In some embodiments, the flow control system comprises a support on which one or more flow control devices are mounted.

The support may be support structure of an integrated perfusion system. The support may be a trolley. All the flow control devices may be mounted on the same support.

In some embodiments, one or more flow control devices are attachable for use on different positions of the support.

In some embodiments, one or more of the flow control devices comprise a housing and the device indicator is comprised at least partially within the housing.

The device indicator may be comprised fully within the housing.

In some embodiments, a portion of the housing is transparent and the device indicator is positioned so as to be noticeable from outside the housing.

In some embodiments, the flow control system comprises one or more of a flow control device for an extracorporeal arterial flow line, a flow control device for a cardioplegia line, a flow control device for a temperature-control fluid line, and/or a flow control device for blood salvage line.

For instance, the flow control system may comprise a first pump for an arterial flow line, a second pump for a cardioplegia line, and a third pump for a blood sucker line. To provide further examples, the flow control system may comprise flow control devices for temperature-control fluid lines, fluid sample offtake lines, hemoconcentrator lines, and other lines.

BRIEF DESCRIPTION OF THE DRAWINGS

Exemplary embodiments of the invention will now be described with reference to the Figures, in which.

DETAILED DESCRIPTION OF SPECIFIC EMBODIMENTS

Figure 1:
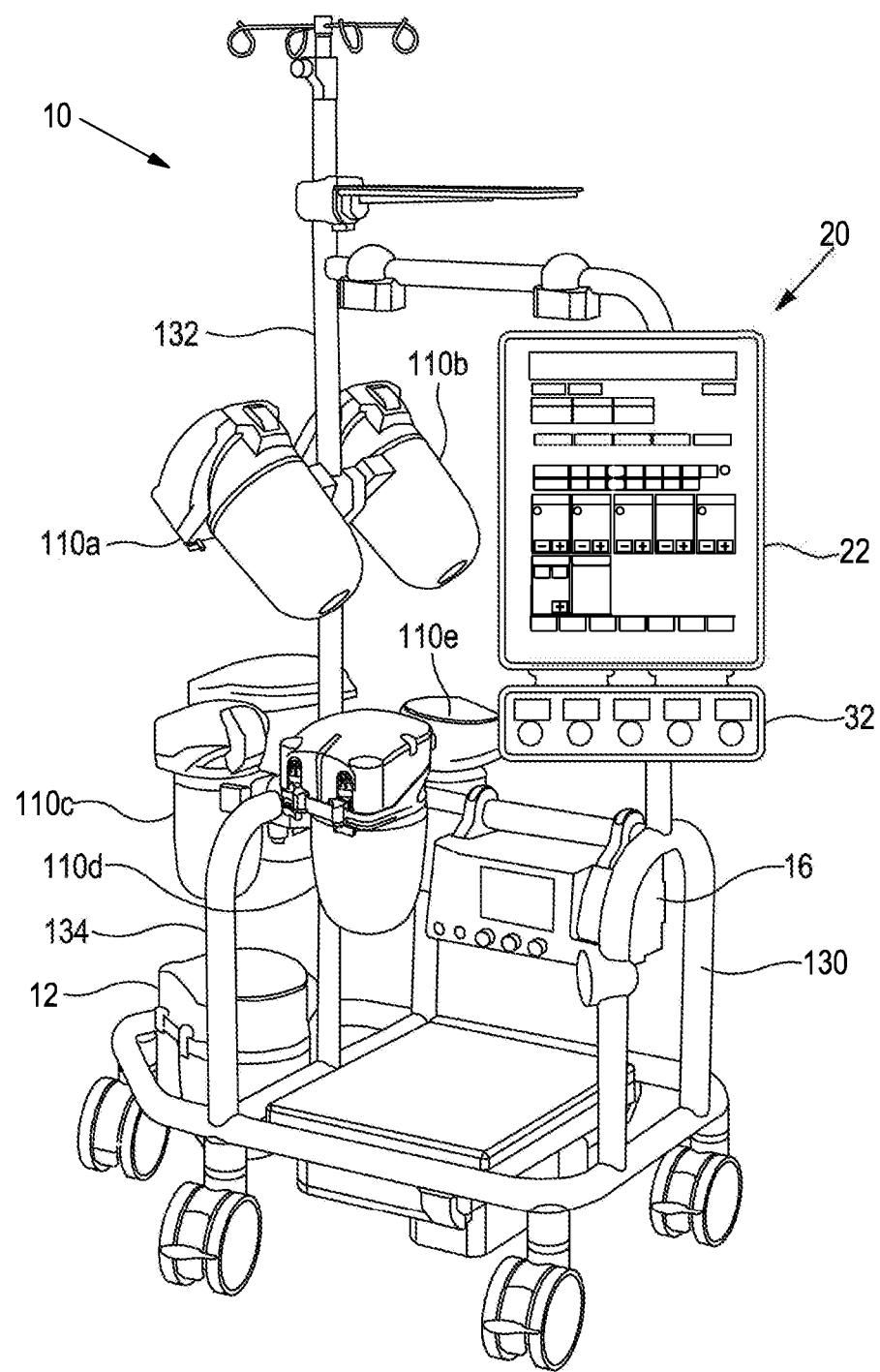
FIG. 1 shows an integrated perfusion system incorporating an embodiment of the present invention.

FIG. 1 shows an integrated perfusion system 10 comprising several components of a perfusion system on a trolley 130. Mounted on the trolley 130 are a venous blood reservoir 12, an oxygenator (not visible in FIG. 1), an oxygenation gas management module 16 comprising a gas supply system and an exhaust gas removal system, and a plurality of pumps 110 (here: five pumps 110a to 110e). Each pump 110 constitutes a flow control device of the invention. In FIG. 1, many elements otherwise present in a complete perfusion system are omitted for clarity. For instance, the components of the perfusion system will be connected by tubing that is not shown in FIG. 1.

The trolley 130 comprises several posts and rails, including a vertical post 132 and horizontal rungs 134. The posts and rails provide a gantry on which the pumps 110 and other components of the perfusion system can be mounted. Each pump 110 can be installed at different locations and in a different orientation, to provide a suitable pump arrangement for the requirements of a particular clinical scenario. The suitability of a pump arrangement may be determined by a type of procedure, condition of a patient, posture of a patient, room available for equipment, number of clinical staff, established practice of a surgical team, and/or personal preference of a user. For instance, in FIG. 1, a first pump 110a and a second pump 110b are mounted on the vertical post 132 and inclined at about 45 degrees. The third pump 110c, the fourth pump 110d and the fifth pump 110e are mounted to the horizontal rungs 134 and positioned upright. The number of pumps, their mounting location and orientation may be completely different.

Each of the pumps comprises an inlet and outlet for a tube to be provided and the pumps are oriented such that the inlet and outlet face away from the trolley. In this configuration each inlet and outlet is easily accessible.

The integrated perfusion system 10 comprises a computer 20 with touch-screen 22. The computer 20 constitutes a controller of the invention and the touch screen 22 constitutes an input interface. The computer 20 may be integrated in the same housing as the input interface or may be provided as a separate unit.

Figure 2:
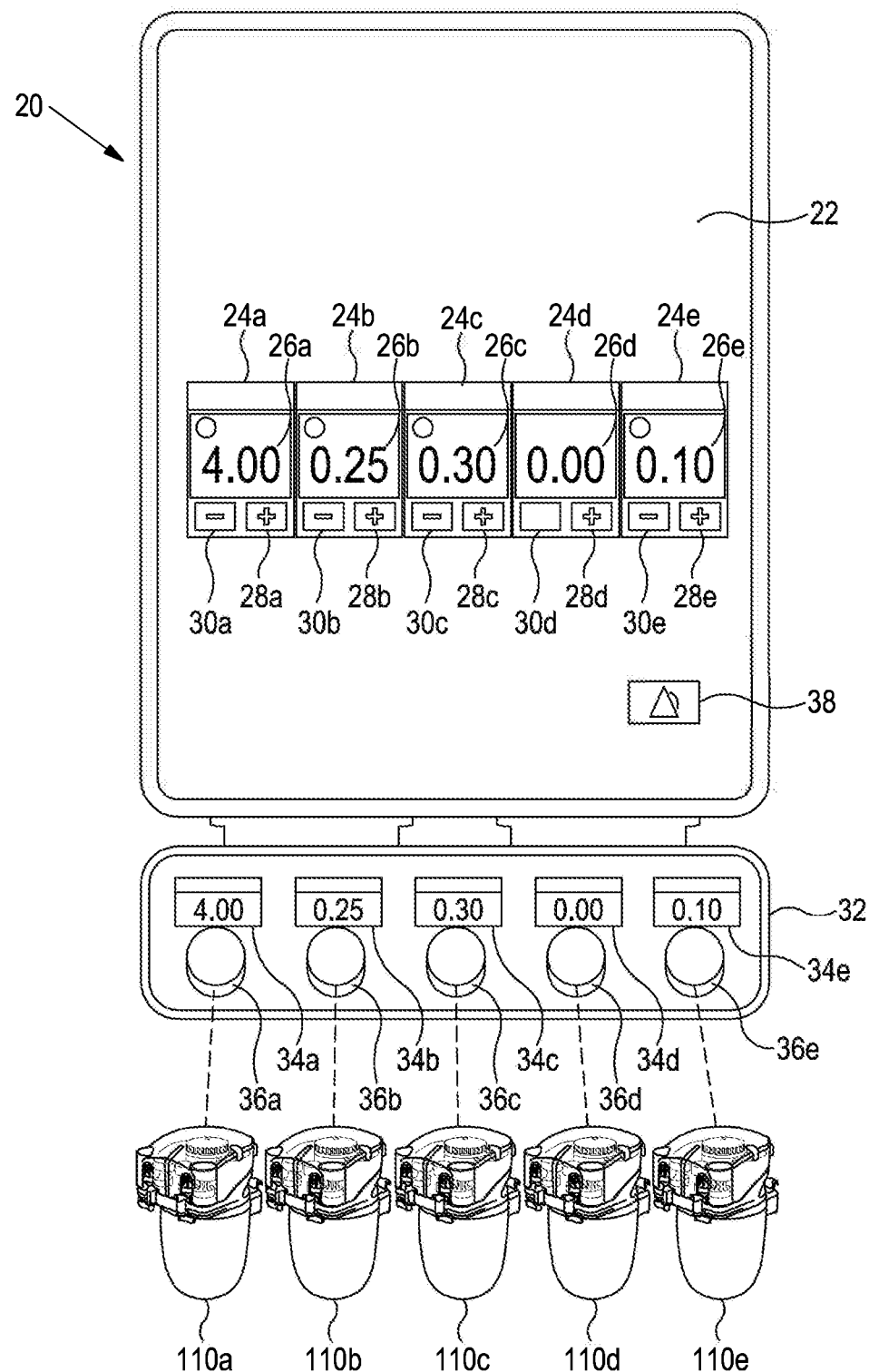
FIG. 2 shows an enlarged view of an input system used with an embodiment of the present invention.

FIG. 2 shows an enlarged view of the touch screen 22 that is a component of the computer 20. Some elements of the user interface visible in FIG. 1 have been omitted, to show selected components of the input interface more clearly. In FIG. 2, the same numerals as in FIG. 1 are used for corresponding elements. FIG. 2 further shows, schematically, five pumps 110a to 110e to illustrate how each pump 110 is controlled by different sections of the input interface. It will be understood that the five pumps 110a to 110e are installed as part of a perfusion system 10, e.g., mounted on a trolley 130 in the manner illustrated in FIG. 1. The pumps may be connected in a different order than that illustrated in FIG. 2.

The touch screen 22 comprises a plurality of individual input elements 24 (here: five input elements 24a to 24e) that can be used to control the operation of the pumps 110. A first input element 24a is provided to control a first pump 110a, a second input element 24b is provided to control a second pump 110b, etc. As part of the input interface, the touch screen 22 comprises, for each pump 110, a display field 26 (here: five display fields 26a to 26e) to display a pump set point. The touch screen 22 further comprises, associated with each display field 26, adjustment keys 28, 30 for increasing a pump set point (here: five increasing adjustment keys 28a to 28e) or decreasing a pump set point (here: five decreasing adjustment keys 30a to 30e, the adjustment key 30d being inactive) of a specific pump 110. For instance, the adjustment keys may be a "plus" or "arrow up" symbol or, correspondingly, a "minus" or "arrow down" symbol.

In addition, the input interface comprises a control station 32. The control station 32 may be a stand-alone unit used instead of a touch screen interface. In the present embodiment, the control station 32 is operatively linked with the touch screen 22. This arrangement provides touch screen input capability as well as a haptic rotary knob input capability.

The control station 32 comprises an array of display fields 34 (here: five display fields 34a to 34e) to display the set point for a specific pump 110a to 110e. The control station 32 comprises a plurality of rotary knobs 36 (here: five rotary knobs 36a to 36e) that can be used to increase or decrease the set point, e.g., by turning a knob clockwise or counter-clockwise. The control station 32 and the touch screen 22 both individually allow the set point for a given pump 110 to be entered either by use of a knob 36, or by using the adjustment keys 28,30 for a specific pump 110. The knobs 36 and adjustment keys 28, 30 constitute input elements of the invention that allow flow control parameters to be set for each one of the pumps 110a to 110e. It will be understood that the input elements on the display fields 26 and 34 are graphical user interfaces and as such the input elements are 'virtual', i.e., the particular position of an input element on the touch screen 22 may be changed by software. The display fields 26 of the touch screen 22 and the display fields 34 of the control station 32 are operatively linked to display the same set point, e.g., as illustrated in FIG. 2, the display field 26a shows a set point value "4.00" for the pump 110a and this is also the set point value "4.00" displayed on the display field 34a. If the rotary knob 36a is used to change the set point indicated on display field 34a, this will also change the set point indicated on display field 26a. Likewise, if the adjustment keys 28a, 30a are used to change the set point, the display field 34a will be updated correspondingly.

The display fields 26 and 34 constitute input interface indicators of the invention. The colour of each display field (e.g., the colour of a frame, a background, or font) can be changed to provide a input status indication. The touch screen 22 comprises a menu button 38 that allows a colour menu to be invoked. By way of the colour menu, a colour of a display field may be set. The colour of corresponding display fields is matched to visually indicate that a display field of the touch screen and of the control station are linked to the same pump. For instance, the colour of the first touch screen display field 26a may be set to 'red' and this will also set the colour of the first control station display field 34a to 'red' to visually indicate that the control fields 26a and 34a relate to the same pump 110a. Likewise, the colour of the second touch screen display field 26b may be set to 'blue' and this will also set the colour of the second control station display field 34b to 'blue'. It will be understood that the colour may be indicated in various ways, on different menu elements. For instance, a display field may be marked in a colour by showing the colour in an area corresponding to a "filled" background element or by a frame element, and/or by displaying the font of a display field in the colour in question. The arrangement allows a different colour to be selected for each one of the five touch screen display fields 26a to 26e and for the control station display fields 34a to 34e.

Figure 3:
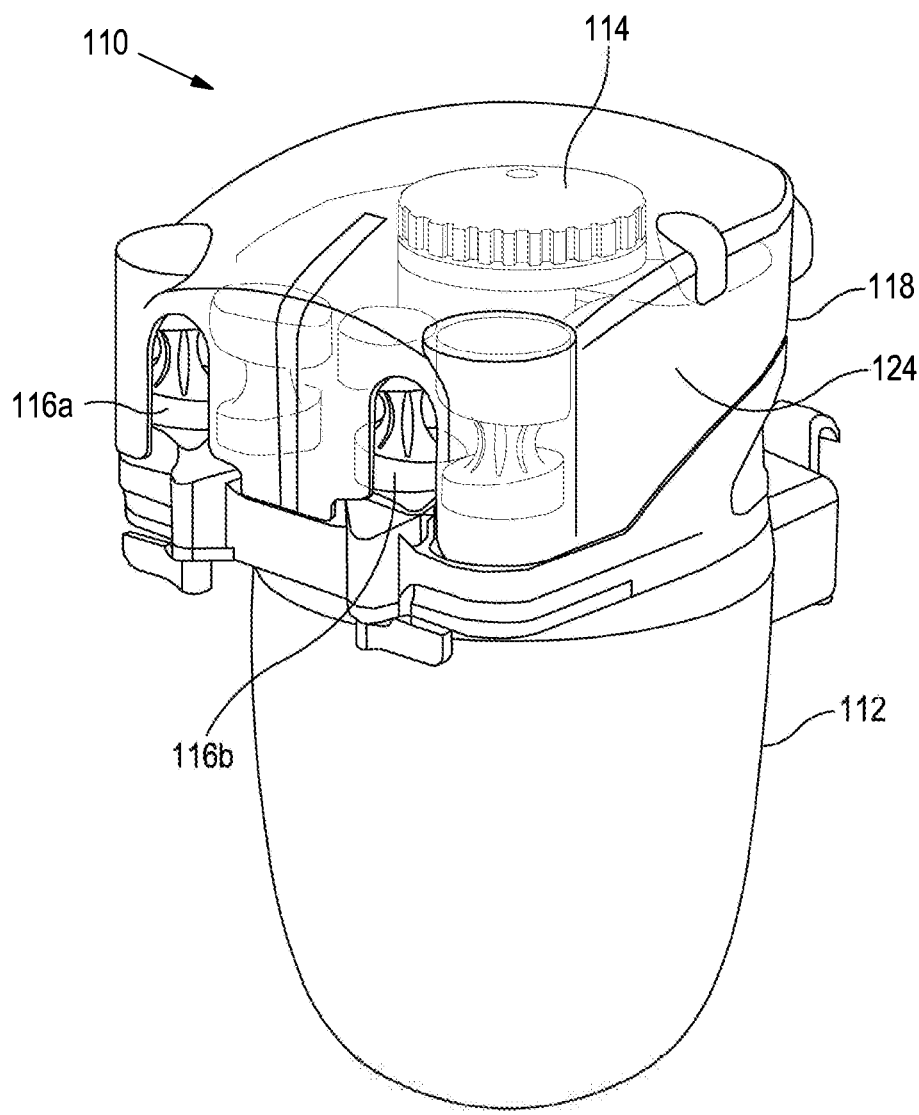
FIG. 3 shows an isometric view of a pump constituting a flow control device used with an embodiment of the present invention.
Figure 4:
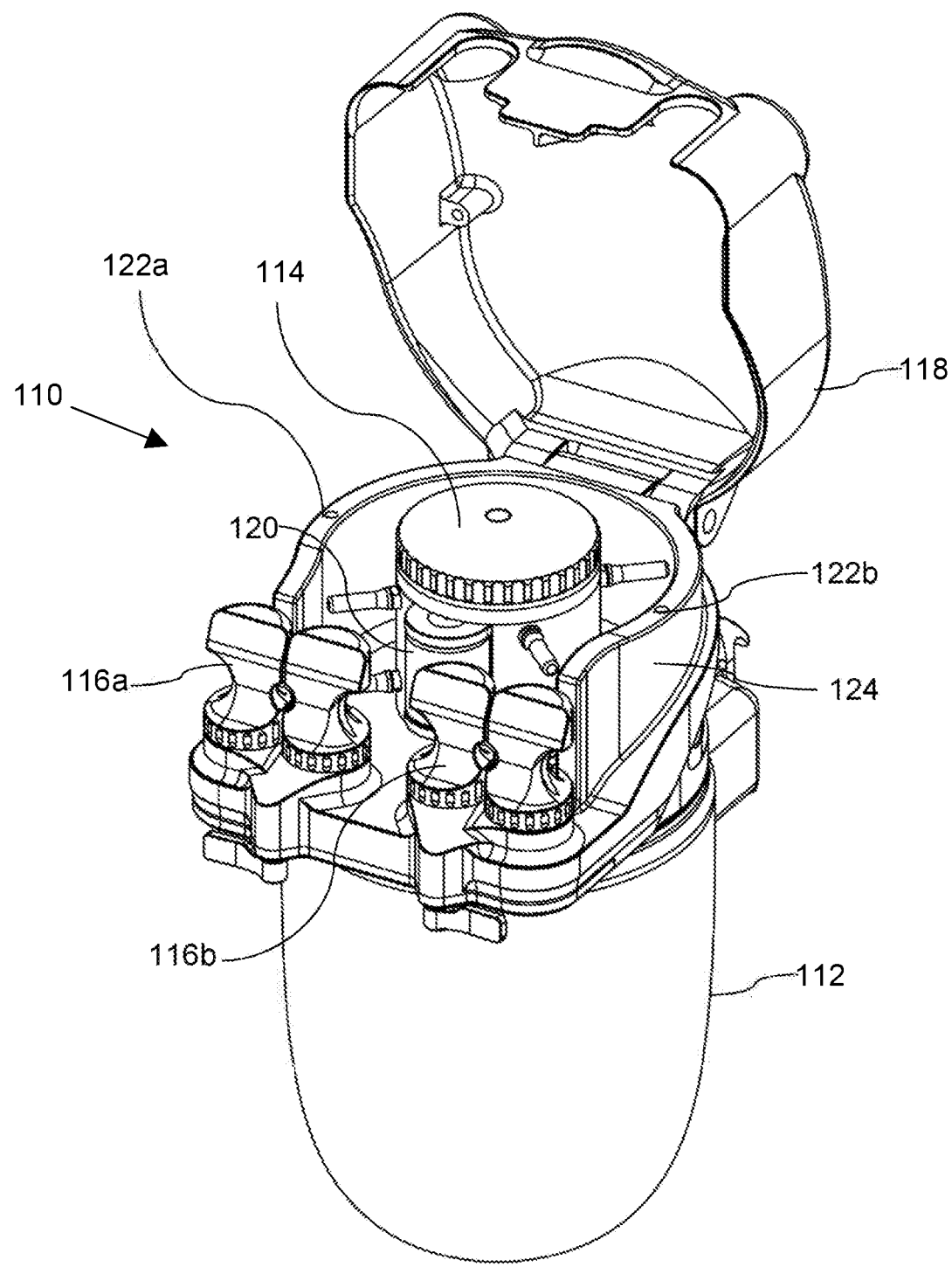
FIG. 4 shows an isometric view of a pump constituting a flow control device used with an embodiment of the present invention.

FIGS. 3 and 4 show an isometric view of a pump 110 corresponding to the pumps 110a-110e illustrated in FIGS.

1 and 2. FIG. 3 shows the pump 110 in a closed-lid condition and FIG. 4 shows the pump 110 in an open-lid condition. The same numerals are used for corresponding components in FIGS. 3 and 4. The pump 110 is a peristaltic pump (roller pump), although other pump types, such as centrifugal pumps may be used in the perfusion system. The pump 110 comprises a housing 112 that contains a drive mechanism 114 (drive mechanism only partially shown in FIGS. 3 and 4), control components for the driving mechanism (not shown in FIG. 3), such as a roller 120 (indicated in FIG. 4), and a tube restraining system comprising a first clamp 116a and a second clamp 116b to securely install a tube to be provided in the pump 110. The housing 112 comprises a lid 118 that can be opened (open in FIG. 4) for insertion of a length of tube and closed (closed in FIG. 3) for the normal operation of the pump. With a length of tube (not shown) inserted, the pump 110 provides a flow passage practically from one clamp 116a of the clamping system to the other clamp 116b of the tube restraining system, along a tube passage indicated by a circumferential wall 124. It is understood that it depends on the flow direction (it whether the drive mechanism 114 rotates clockwise or anti-clockwise) whether a clamp side constitutes an inlet or an outlet.

The lid 118 is transparent to permit visual inspection of some of the inner pump components even when the lid 118 is closed. As shown in FIG. 3, due to the transparency of the lid 118, the clamps 116a and 116b and part of the driving mechanism 114 are visible. In use, a length of tubing extending through the pump 110 and the roller pump actuators can be seen through the transparent lid 118. Inspection of these components provides immediate visual feedback on the function of a pump, i.e., whether or not the rollers 120 (FIG. 4) of the drive mechanism rotate. However, in practice it can be challenging to discern, quickly, in which direction the rollers rotate, or what their rotational speed is, so that an operator may have to observe a pump 110 for some time (in the regions of a few seconds or longer) to reassure himself of the direction.

Turning to FIG. 4, inside the lid 118 there is a LED arrangement 122 constituting an indicator arrangement of the invention. The LED arrangement 122 comprises one or more (here: two LEDs 122a and 122b) multi-colour LEDs constituting device indicators that can be controlled to emit light in one of a range of colours. The LEDs 122a and 122b are integrated with the wall 124 of the tube passage and flush with wall surface so as to avoid any interference with the mechanical operation of the rollers 120. A first LED 122a is positioned on a portion of the wall 124 closer to one clamp 116a and the second LED 122b is position on the wall a portion of the wall 124 closer to the other clamp 116b, and by way of the proximity each LED 122a and 122b is associated with one side of the pump passage. Thereby, the LEDs 122a and 122b are located within the lid 118 of the housing 112 and noticeable from outside the housing 118.

For practical purposes, it is considered herein that LEDs 122a, 122b can be programmed to emit any colour from the visible spectrum or selected from a large selection of colours. Each LED is controllable by the controller to emit one of these colours. When one or both LEDs 122a, 122b of the LED arrangement 122 are activated by the controller to emit light in a particular colour, the transparent lid 118 is illuminated from within, and appears to be lit in the particular colour.

The transparent lid 118 will scatter a portion of the light emitted from a LED internally and other portions of the light emitted from the LED will be transmitted through the lid 118, so as to provide light emission in multiple directions.

The transparent housing may comprise a scatter-increasing configuration to improve the light throw from the lid 118. It is understood that the light emitted from the LED is not primarily intended for illumination purposes but it is of intensity strong enough to be clearly visible in a brightly illuminated operating theatre. The LEDs constitute solid state lighting devices of the indicator arrangement.

The set point for a particular pump 110 may be set by via the input interface, e.g., via a corresponding adjustment key 28, 30 and/or via a corresponding rotary knob 36. By way of the invention, the LED colour of the particular pump 110 is set to the colour of the touch screen display field 26 corresponding to a particular pump 110 and/or the control station display field 34 for the same pump 110. This allows different colours to be set for different pumps, while ensuring that the same colour is used for a specific pump and for the input interface elements controlling a set point of the same specific pump.

The invention facilitates a quick visual control of the pump operation when a set point is changed for a specific pump e.g., 110a of many pumps of the perfusion system. A few of the pumps e.g., 110b, 110c of the perfusion system may be operating in an automated or semi-automated mode, for instance in a closed loop control mode. These pumps 110b, 110c, may start or stop their operation coincidentally at the same time as the set point is changed for a specific pump 110a.

The indicator arrangement facilitates a quick visual check, such as whether or not a specific pump is operating as expected, i.e., whether or not a specific pump is starting to operate, or stopping to operate, or increasing speed, or decreasing speed, as expected, in response to a new set point entered at the user interface for the specific pump. The quick visual check is facilitated because the input status indication for a particular display field may have one colour, and the pump lit in that colour is the pump controlled by the particular display field. The user is not distracted as much as would otherwise be the case by having to reassure himself that he is looking at the right pump, because the pump can be identified by the indicator arrangement. In particular, the invention allows colour blind users to select indicator colours that correspond to a colour spectrum they can discern. For instance, users affected by protanopia (a condition affecting red vision) may select an indicator colour configuration for each one of the pumps 110a to 110e that avoids red light.

The provision of a look-up table allowing colour tones to be synchronized so as to have a closer colour match between the device indicators and the input interface indicators further improves the suitability for colour vision deficiency. It can be imagined that, for an exemplary setup with five pumps 110a to 110e, a full colour spectrum allows different colours to be assigned easily (e.g., red, green, blue, yellow, and white), and in that case, an exact colour match may not be regarded as particularly beneficial. However, if colours have to be assigned from a limited spectrum, e.g., using only yellow tones and blue tones, the colour tone synchronization is helpful to ensure that close colours are clearly distinguishable when used with different light emitting elements. Likewise, if, for regulatory reasons, certain colours may only be used for predefined conditions (e.g., the colour red may be reserved for an alarm condition), this further improves the availability of remaining colours. The advantage increases with the number of flow control devices operated via the input interface.

The flow control devices are provided with device indicators able to display a plurality of device indications. For instance, the device indicators can display one colour at a time, and can switch to display another colour. The indicators of each pump may indicate different colours. The device indicator can be positioned in a way to optimise the number of viewing angles and positions from which the indications are visible. This can, for example, be achieved by placing the indicators around a circumference of the flow control device, on the top surface of the flow control device, or both on the top and around the circumference of the flow control device. In embodiments, a single LED or an arrangement of two LEDs for each pump may suffice to ensure good visibility.

The indicator arrangement of one pump may consist of two device indicators (e.g., two independently actuatable solid state devices) indicating a flow direction on the pump. In this regard, pump rotors may operate at high speeds, and while it is possible to see the pump rotating, it may be more difficult to quickly discern the direction (e.g., forward or backward), particularly if the pump is not seen from above. For instance, in the configuration illustrated in FIG. 1, an operator standing in front of the touch screen 22 will not be able to easily see the drive mechanism of the pumps 110a and 110b, because the pumps 110a and 110b face away from the screen touch screen 22. The device indicators may be set up to indicate a forward flow and a reverse flow by using a continuously lit LED at the upstream side of the pump passage and a flashing LED at the downstream side of the pump passage. Using the example of FIG. 1, it can be imagined that an operator standing at the touch screen 22 can more easily discern quickly in which manner one of the pumps 110a or 110b is illuminated, rather than having to gain reassurance in which manner the driving mechanism operates, as this may not be readily visible to an operator standing at the touch screen 22 (and is not visible in FIG. 1).

The flow control system may comprise a configuration preventing the use of one or more predetermined colours for a pump. One colour may be reserved for an alarm condition, and one colour may be reserved for a warning condition. In that case, the colour menu may automatically deselect or remove from the menu colour options any colours reserved for other purposes.

The flow control system may comprise a configuration preventing the use of the same colour for two or more pumps. The colour menu may automatically deselect or remove from the menu options any colours already assigned to another pump.

What is claimed is:

1. A flow control system comprising:
   one or more flow control devices of a clinical perfusion system, each flow control device capable of controlling, according to flow rate parameters provided by the flow control system, a flow rate of a fluid to be provided;
   an input interface including at least one input element for each one of the flow control devices permitting flow control parameters to be set for the flow control device, thereby to control said flow rates of the fluids to be provided; and
   an indicator arrangement including:
      a device indicator on each flow control device, wherein the device indicator is capable of displaying a plurality of colours,
      the one or more device indicators are capable of providing a plurality of indications,
      the one or more device indicators are controllable by the flow control system to provide one indication of the plurality of indications to indicate an active condition of the flow control device, and wherein the one indication can be a display of a particular one of the colours,
      the one or more device indicators are configurable by the control system independently of the flow rate parameter, thereby to allow the indication provided by the device indicator to be adjusted for different clinical environments regardless of flow rate parameters issued to the one or more flow control devices; and
      an input interface indicator on the input interface to provide an input status indication corresponding to an input status of the flow control parameters set by the one or more input elements, and the indicator arrangement is configured to use an input status indication for at least one input element displayed in a colour that matches the particular colour displayed by the device indicator of the flow control device whose flow control parameters are set by the at least one input element.

2. The flow control system according to claim 1, wherein the device indicator comprises one or more solid state lighting devices.

3. The flow control system according to claim 1, wherein the indicator arrangement is configured to indicate the flow direction of the fluid to be provided.

4. The flow control system according to claim 3, wherein at least one flow control device comprises a first device indicator and a second device indicator, to indicate the flow direction by using the first device indicator to provide a first device indication and the second device indicator to provide a second device indication, wherein the second device indication differs from the first device indication.

5. The flow control system according to claim 4, wherein the second device differs from the first device indication by providing at least one distinction from the group comprising a: different intensity, a different colour, and a different time-dependent signal.

6. The flow control system according to claim 1, wherein the indicator arrangement comprises a controller comprising a processor and software instructions implemented by the processor.

7. The flow control system according to claim 1, wherein the input interface comprises a configuration identifying an input element by a colour.

8. The flow control system according to claim 1, comprising a lookup table comprising data for colour control signals to better match colour tones of the one or more device indicators with corresponding colour tones of the input interface indicator, thereby to provide a better colour match between indicator arrangements using different indicator device types.

9. The flow control system according to claim 8, wherein the input interface comprises a touch screen.

10. The flow control system according to claim 1, further comprising a support on which one or more flow control devices are mounted.

11. The flow control system according to claim 10, wherein at least one flow control device is attachable for use on different positions of the support.

12. The flow control system according to claim 1, wherein at least one flow control device comprises a housing and wherein the device indicator is comprised at least partially within the housing.

13. The flow control system according to claim 12, wherein a portion of the housing is transparent and wherein the device indicator is positioned so as to be noticeable from outside the housing.

14. The flow control system according to claim 1, comprising at least one device from the group comprising: a flow control device for an extracorporeal arterial flow line, a flow control device for a cardioplegia line, a flow control device for a temperature-control fluid line, and a flow control device for blood salvage line.

* * * * *